United States Patent
Gu et al.

(10) Patent No.: US 11,065,189 B2
(45) Date of Patent: Jul. 20, 2021

(54) LIQUID PERSONAL CLEANSING COMPOSITION

(71) Applicant: Conopco, Inc., Englewood Cliffs, NJ (US)

(72) Inventors: Yeyi Gu, Shanghai (CN); Tirucherai Varahan Vasudevan, Bethany, CT (US); Kayla Marie Kemler, Shelton, CT (US); Adrienne Lyn King, Stamford, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 16/470,500

(22) PCT Filed: Dec. 13, 2017

(86) PCT No.: PCT/EP2017/082680
§ 371 (c)(1),
(2) Date: Jun. 17, 2019

(87) PCT Pub. No.: WO2018/114536
PCT Pub. Date: Jun. 28, 2018

(65) Prior Publication Data
US 2020/0085713 A1    Mar. 19, 2020

(30) Foreign Application Priority Data
Dec. 21, 2016    (WO) ............... PCT/CN2016/111309
Feb. 8, 2017    (EP) .................................... 17155150

(51) Int. Cl.
| C11D 1/88 | (2006.01) |
| A61K 8/44 | (2006.01) |
| A61K 8/36 | (2006.01) |
| A61K 8/73 | (2006.01) |
| A61Q 19/10 | (2006.01) |

(52) U.S. Cl.
CPC ............... *A61K 8/442* (2013.01); *A61K 8/36* (2013.01); *A61K 8/44* (2013.01); *A61K 8/731* (2013.01); *A61K 8/737* (2013.01); *A61Q 19/10* (2013.01)

(58) Field of Classification Search
CPC .... C11D 1/88; C11D 1/90; C11D 1/94; C11D 3/0094; C11D 3/2079; C11D 3/30; C11D 3/3917; C11D 7/3254
See application file for complete search history.

(56) References Cited

U.S. PATENT DOCUMENTS

| 2004/0022748 A1* | 2/2004 | Ananthapadmanabhan ................ A61K 8/463 424/61 |
| 2006/0111258 A1* | 5/2006 | Tobita .................... A61Q 19/10 510/130 |
| 2007/0213244 A1* | 9/2007 | Tobita .................... A61Q 19/10 510/130 |
| 2008/0008672 A1* | 1/2008 | Tobita .................... C11D 1/835 424/70.1 |
| 2012/0009127 A1 | 1/2012 | Dasgupta et al. |
| 2013/0252853 A1* | 9/2013 | Gayral Chirac ......... C09K 8/52 507/102 |
| 2015/0297489 A1* | 10/2015 | Kleinen ................... C11D 1/94 514/785 |
| 2015/0306044 A1 | 10/2015 | Gupta et al. |
| 2015/0315123 A1* | 11/2015 | Schuch .................. A61Q 15/00 514/786 |
| 2017/0137366 A1* | 5/2017 | Schuch .................. A61Q 19/10 |
| 2017/0218120 A1* | 8/2017 | Brandt ..................... A61K 8/86 |

FOREIGN PATENT DOCUMENTS

| CN | 103479529 | 1/2014 |
| CN | 103479532 | 1/2014 |
| EP | 2786742 | 10/2014 |
| WO | WO2015071298 | 5/2015 |

OTHER PUBLICATIONS

Intense Nourishment Shower Foam; Mintel GNPD; 2017; pp. 1-3; XP002769178.
Written Opinion in PCTEP2017082680; dated Nov. 2, 2018.
Written Opinion 2 in PCTEP2017082680; dated Mar. 18, 2019.
Search Report in PCTEP2017082680; dated Apr. 5, 2018.
Search Report and Written Opinion in EP17155150; dated May 2, 2017.

\* cited by examiner

*Primary Examiner* — Charles I Boyer
(74) *Attorney, Agent, or Firm* — Edward A. Squillante, Jr.

(57) ABSTRACT

The invention relates to aqueous skin cleansing compositions. Specific amounts and chain length of acyl glycinate and acyl glutamate when used in specified ratios, have been found to unexpectedly enhance lather volume and texture, as well as provide superior mildness.

10 Claims, No Drawings

LIQUID PERSONAL CLEANSING COMPOSITION

BACKGROUND OF THE INVENTION

Field of the Invention

The present invention relates to aqueous skin cleansing compositions suitable for topical application for cleansing the human body, such as the skin and hair. In particular, it relates to compositions which are preferably sulfate free personal cleansing compositions that are able to lather appreciably, are stable and are mild.

Background of the Art

Consumers seek personal cleansing compositions that are stable, extremely mild and moisturizing while delivering superior sensory benefits such as creamy lather and soft, smooth skin typically after one shower. Soap-based skin cleansing formulas are well known for their high lather; however, such formulations are generally harsher to the skin than synthetic surfactant, non-soap based formulations.

It was unexpectedly determined that specific combinations of two amino acid-based synthetic surfactants i.e. acyl glycinate and acyl glutamate, each with specific alkyl chain distributions, demonstrated a superior lather profile of soap based formulations in combination with or free from soap based surfactants. Further, the compositions are much milder (measure by stearic acid replenishment and/or protein damage caused) than compositions that may have similar lather, but comprise higher amounts of soap.

The inventive combinations may be used in a wide variety of skin cleansing products including, but not limited to, soap-synthetic detergent formulations and soap-free synthetic detergent formulations.

Many references disclose broadly possible combinations of acyl glycinate and acyl glutamate surfactants. Applicants are aware of none however, which disclose the unexpected synergy when combining specific chain length combinations of acyl glycinate and acyl glutamate. Applicants are further not aware of compositions having these combinations at specific ratios and used further with lower levels of soap to provide milder compositions which lather as well as those with more soap (e.g., 15% by wt and higher).

Database GNPD MINTEL; January 2017 (2017-01), intense nourishment shower foam", XP00269178 disclose a shower foam containing sodium lauroyl glutamate and sodium lauroyl glycinate.

EP2786742A1 relates to cosmetics containing rhamnolipids.

CN103479529A discloses a surfactant composition.

CN103479532A discloses a surfactant composition

WO 2015/071298 (L'Oreal), for example, disclose compositions comprising at least one acyl glycinate type surfactant and which may also contain acyl glutamate (page 5, line 17). There is no disclosure of synergy between specific amounts of specific chain length materials, particularly with regard to enhanced lather volume or texture.

U.S. 2015/0306044 discloses mild antibacterial cleansing compositions which may contain alkyl glycinate, acyl glutamate or mixtures thereof. Again, there is no disclosure of synergy between specific combinations of chain lengths of acyl glycinate and acyl glutamate used at specific ratios.

There are also several products marketed in Japan (products and compositions listed in Table A) that contain mixtures of acyl glycinate and acyl glutamate surfactants. Here again, there is no recognition that a mixture a specific chain length combinations of acyl glycinates and acyl glutamates used at specific ratios can provide enhanced synergistic lather performance while maintaining mildness.

TABLE A

| Competitor Product | Wt % Cocoyl glycinate | Wt % cocoyl glutamate |
|---|---|---|
| Care Cera Bodywash | 1.13 | 2.44 |
| FANCI Bodywash Moisturizing | 4.0 | 1.57 |
| Three Full Bodywash | 6.96 | 3.14 |
| DHC Men Bodywash | 0.25 | 0.75 |

Analysis conducted at Unilever laboratory in Trumbull, Conn., USA

BRIEF DESCRIPTION OF THE INVENTION

One aspect of the invention is an aqueous skin cleansing composition comprising:
a) 0.1 to 30%, preferably 0.5 to 25%, more preferably 1 to 20% and most preferably 2 to 10 to % by wt. of either individual surfactants or mixtures of $C_{10}$, $C_{12}$ and $C_{14}$ acyl glycinates;
b) 0.1 to 30%, preferably 0.5 to 25%, more preferably 1 to 20% and most preferably 5 to 15 by wt. $C_{14}$ acyl glutamate (that is, composition may comprise mixture of $C_{14}$ acyl glutamate and only $C_{10}$ acyl glycinate, $C_{12}$ acyl glycinate or $C_{14}$ acyl glycinate; a mixture of $C_{14}$ acyl glutamate with both $C_{10}$ acyl glycinate and $C_{12}$ acyl glycinate; or with $C_{12}$ acyl glycinate and $C_{14}$ acyl glycinate, etc.)
in combination with other anionic, non-ionic and amphoteric/zwitter ionic surfactants wherein the ratio of $C_{14}$ acyl glutamate to acyl glycinate is 0.6 to 12.5, preferably 0.6 to 10, more preferably 0.7 to 7.5 and most preferably 0.8 to 5 for $C_{10}$ acyl glycinate (when present), 0.02 to 4, preferably 0.04 to 3.5, more preferably 0.06 to 3.0 and most preferably 0.08 to 2.7 for $C_{12}$ acyl glycinate (when present), 0.6 to 5, preferably 0.8 to 4.5, more preferably 1 to 4 and most preferably 1.2 to 3.7 for $C_{14}$ acyl glycinate (when present) or mixtures thereof in those specific ratios (when two or more glycinates are present).

A preferred mixture comprises 0.1 to 30%, preferably 1 to 25%, more preferably 2 to 20% and most preferably 5 to 15 wt % $C_{14}$ acyl glutamate and 0.1 to 30%, preferably 0.5 to 25%, more preferably 1 to 20% and most preferably 2 to 10% by wt of $C_{10}$ acyl glycinate where ratio of $C_{14}$ acyl glutamate to $C_{10}$ acyl glycinate is 0.5 to 12.5, preferably 0.6 to 10, more preferably 0.7 to 7.5 and most preferably 0.8 to 5.

Another preferred mixture is mixture of 1 to 30%, preferably 1 to 25%, more preferably 2 to 20% and most preferably 5 to 15% by wt of $C_{14}$ acyl glutamate and 0.1 to 30%, preferably 0.5 to 25%, more preferably 1 to 20% and most preferably 2 to 15% by wt of $C_{12}$ acyl glycinate where ratio of $C_{14}$ acyl glutamate to $C_{12}$ acyl glycinate is 0.02 to 4, preferably 0.04 to 3.5, more preferably 0.06 to 3 and most preferably 0.08 to 2.7.

Yet another preferred mixture is mixture of 0.1 to 30%, preferably 1 to 25% $C_{14}$ acyl glutamate and 1 to 30%, preferably 1 to 25% $C_{14}$ acyl glycinate where ratio of $C_{14}$ acyl glutamate to $C_{14}$ glycinate is 0.6 to 5, preferably 0.8 to 4.5, more preferably 1 to 4 and most preferably 1.2 to 3.7.

Preferably, compositions according to this aspect of the invention have lather volume greater than 300 ml, as measured by protocol defined in protocol section.

Preferred compositions of this aspect of the invention have lather texture greater than 20 grams, as measured by protocol described later in the specification.

In another aspect, the invention comprises:
a) 0.1 to 20%, preferably 0.5 to 15% and more preferably 1 to 10% by wt of individual surfactants or mixtures of $C_{10}$, $C_{12}$ and $C_{14}$ acyl glycinates;
b) 0.1 to 20%, preferably 0.5 to 15% and more preferably 1 to 10% by wt of individual surfactants or mixtures of $C_{14}$ acyl glutamate (again, $C_{14}$ acyl glutamate is preferred with one or more of the $C_{10}$, $C_{12}$ and $C_{14}$ acyl glycinates);
c) 1 to 25%, preferably 5 to 20% and more preferably 10 to 15% by wt of $C_8$ to $C_{24}$ fatty acid soap, preferably $C_{10}$ to $C_{20}$ fatty acid soap, more preferably $C_{12}$ to $C_{16}$ soap and most preferably $C_{12}$ to $C_{14}$ fatty acid soap
   in combination with other anionic, non-ionic and amphoteric/zwitter ionic surfactants, where in the ratio of $C_{14}$ acyl glutamate to $C_{10-14}$ acyl glycinate or $C_{12}$ acyl glycinate is 0.01 to 5, preferably 0.1 to 4.5, more preferably 0.5 to 4 and most preferably 1.5 to 3.5.

In a preferred embodiment, the mix of $C_{10}$, $C_{12}$ and $C_{14}$ acyl glycinate used with $C_{14}$ acyl glutamate is in the range of 1 to 20%, preferably 5 to 15% $C_{10}$ acyl glycinate, 60 to 90%, preferably 65 to 85% $C_{12}$ acyl glycinate and 5 to 25%, preferably 10 to 20% $C_{14}$ acyl glycinate. As indicated, one or two or all three may be used.

Unexpectedly, applicants have found that specific amounts and chain length combinations of acyl glycinates and acyl glutamates, preferably used in specified ratios, lead to enhanced lather volume and texture generally; as well as superior mildness (as measured by higher stearic acid replenishment and lower protein damage) relative to compositions having higher amounts of soap in the formulation (e.g., if used in lower soap formulations defined in the last aspect of our invention). Thus, in such compositions, applicants can match the high lather normally associated with higher soap while avoiding harshness issues also associated with soap. As noted, in its broadest aspect, compositions need not contain soap.

In another form, the invention also provides a method for enhancing lather (e.g., to match or surpass that of a higher soap formulation) while maintaining excellent mildness (measured as noted above).

DETAILED DESCRIPTION OF THE INVENTION

In one aspect of the invention is an aqueous skin cleansing composition comprising:
a) 0.1 to 30% preferably, 1 to 25% and more preferably 5 to 20% by wt. of either individual surfactants or mixtures of $C_{10}$, $C_{12}$ and $C_{14}$ acyl glycinates;
b) 0.1 to 30% preferably 1 to 25% and more preferably 5 to 20% by wt. $C_{14}$ acyl glutamate
   in combination with other anionic, non-ionic and amphoteric/zwitter ionic surfactants, wherein the ratio of $C_{14}$ acyl glutamate to acyl glycinate is 0.6 to 12.5, preferably 0.6 to 10, more preferably 0.7 to 7.5 and most preferably 0.8 to 5 for $C_{10}$ acyl glycinate (when present), 0.02 to 4, preferably 0.04 to 3.5, more preferably 0.06 to 3.0 and most preferably 0.08 to 2.7 for $C_{12}$ acyl glycinate (when present), 0.6 to 5, preferably 0.8 to 4.5, more preferably 1 to 4 and most preferably 1.2 to 3.7 for $C_{14}$ acyl glycinate (when present) or mixtures thereof in those specific ratios (when two or more acyl glycinates are present).

A preferred mixture comprises 0.1 to 30%, preferably 1 to 25%, more preferably 2 to 20% and most preferably 5 to 15 wt % $C_{14}$ acyl glutamate and 0.1 to 30%, preferably 0.5 to 25%, more preferably 1 to 20% and most preferably 2 to 10% by wt of $C_{10}$ acyl glycinate where ratio of $C_{14}$ acyl glutamate to $C_{10}$ acyl glycinate is 0.5 to 12.5, preferably 0.6 to 10, more preferably 0.7 to 7.5 and most preferably 0.8 to 5.

Another preferred mixture is mixture of 1 to 30%, preferably 1 to 25%, more preferably 2 to 20% and most preferably 5 to 15% by wt of $C_{14}$ acyl glutamate and 0.1 to 30%, preferably 0.5 to 25%, more preferably 1 to 20% and most preferably 2 to 15% by wt of $C_{12}$ acyl glycinate where ratio of $C_{14}$ acyl glutamate to $C_{12}$ acyl glycinate is 0.02 to 4, preferably 0.04 to 3.5, more preferably 0.06 to 3 and most preferably 0.08 to 2.7.

Yet another preferred mixture is mixture of 0.1 to 30%, preferably 1 to 25% $C_{14}$ acyl glutamate and 1 to 30%, preferably 1 to 25% $C_{14}$ acyl glycinate where ratio of $C_{14}$ acyl glutamate to $C_{14}$ acyl glycinate is 0.6 to 5, preferably 0.8 to 4.5, more preferably 1 to 4 and most preferably 1.2 to 3.7.

Preferably, compositions according to this aspect of the invention have lather volume greater than 300 ml, as measured by protocol defined in protocol section.

Preferred compositions of this aspect of the invention have lather texture greater than 20 grams, as measured by protocol below.

In another aspect, the invention comprises:
a) 0.1 to 20%, preferably 0.5 to 15% and more preferably 1 to 10% by wt of individual surfactants or mixtures of $C_{10}$, $C_{12}$ and $C_{14}$ acyl glycinates;
b) 0.1 to 20%, preferably 0.5 to 15% and more preferably 1 to 10% by wt of individual surfactants or mixtures of $C_{14}$ acyl glutamate;
c) 1 to 25%, preferably 5 to 20% and more preferably 10 to 15% by wt of $C_8$ to $C_{24}$ fatty acid soap, preferably $C_{10}$ to $C_{20}$ fatty acid soap, more preferably 012 to $C_{16}$ soap and most preferably $C_{12}$ to $C_{14}$ fatty acid soap
   in combination with other anionic, non-ionic and amphoteric/zwitter ionic surfactants, where in the ratio of $C_{14}$ acyl glutamate to $C_{10-14}$ acyl glycinate or $C_{12}$ acyl glycinate is 0.01 to 5, preferably 0.1 to 4.5, more preferably 0.5 to 4 and most preferably 1.5 to 3.5.

In a preferred embodiment, the mix of $C_{10}$, $C_{12}$ and $C_{14}$ acyl glycinate used with $C_{14}$ acyl glutamate is in the range of 1 to 20%, preferably 5 to 15% $C_{10}$ acyl glycinate, 60 to 90%, preferably 65 to 85% $C_{12}$ acyl glycinate and 5 to 25%, preferably 10 to 20% $C_{14}$ acyl glycinate. As indicated, one or two or all three may be used.

Unexpectedly, applicants have found that specific amounts and chain length combinations of acyl glycinates and acyl glutamates lead to enhanced lather volume and texture generally; as well as superior mildness (as measured by higher stearic acid replenishment and lower protein damage) relative to compositions having higher amounts of soap in the formulation (e.g., if used in lower soap formulations defined in the last aspect of our invention). Thus, in such compositions, applicants can match the high lather normally associated with higher soap while avoiding harshness issues also associated with soap. As noted, in its broadest aspect, compositions need not contain soap.

In another form, the invention also provides a method for enhancing lather (e.g., to match or surpass that of a higher soap formulation) while maintaining excellent mildness (measured as noted above).

Surfactants:

a) Mild anionic surfactants are preferably included in inventive cleansing composition in addition to the claimed acyl glycinate and acyl glutamate surfactants. Preferably sulfate containing surfactants and soaps are present at levels below 3, 2 or 1 wt. % and preferably are not present at all in the broadest aspect. However, as noted, in one aspect, the compositions are low soap compositions which comprise 1 to 25%, preferably 5 to 20% and more preferably 10 to 15% by wt of $C_8$ to $C_{24}$ fatty acid soap, more preferably $C_{10}$ to $C_{20}$ fatty acid soap and most preferably $C_{12}$ to $C_{18}$ fatty acid soap. Surfactants are compounds that have hydrophobic and hydrophilic portions that act to reduce the surface tension of the aqueous solutions they are dissolved in. Other useful surfactants include, but are not limited to, sulfosuccinates, sarcosinates, taurates, alaninates and threoninates. Preferably, harsh sulfate containing anionic surfactants such as SLES, SLS, Sodium Trideceth Sulfate, and soaps and blends thereof are present at maximum concentration levels of 3, 2 or 1 wt % and are preferably absent from the composition of syndet based surfactants.

Anionic Surfactants:

The cleansing composition of the present invention preferably contains one or more additional non-soap, mild synthetic anionic detergents. Total mild synthetic anionic surfactants are preferably used at levels as low as 5, 4, 3 or 2% by wt. and at levels as high as 8, 12, 16 or 20% by wt.

In one preferred form, acyl glycinates and acyl glutamates are present as primary surfactant (50% or more of surfactant system) and comprise 0.1 to 25%, 0.5 to 15% and more preferably 1 to 10% by wt. of either individual surfactants or mixtures of $C_{10}$, $C_{12}$ and $C_{14}$ acyl glycinates and 0.1 to 25%, 0.5 to 15% and more preferably 1 to 10% by wt. $C_{14}$ acyl glutamate. The $C_{14}$ acyl glutamate is present in defined ratios relative to the different chain length acyl glycinates, whether only one acyl glycinate or mixture of acyl glycinates are used.

In another form, the composition is a low soap composition where $C_{10-14}$ acyl glycinate and $C_{14}$ acyl glutamate are present as primary non-soap surfactant (comprise 50% or more of any other non-soap surfactant present).

Solubilizing cations such as sodium, potassium, ammonium or substituted ammonium may be used. Sodium and potassium are preferred.

The inventive cleansing composition contains as noted $C_{10}$ to $C_{14}$ acyl glycinates. This surfactant may be prepared by reaction of $C_{10}$ to $C_{14}$ fatty acid chloride with glycine in the presence of sodium, potassium, or ammonium hydroxide to form the corresponding acyl glycinate.

In general, the acyl glycinate may be present at levels of 0.1% to 25% by wt., preferably 0.1 to 20%, preferably 0.5 to 15% and more preferably 1 to 10% by wt.

The inventive cleansing composition also contains $C_{14}$ acyl glutamate. This surfactant may be prepared by reaction of $C_{14}$ fatty acid chloride with glutamic acid in the presence of sodium, potassium, or ammonium hydroxide to form the corresponding $C_{14}$ acyl glutamate.

The acyl glutamate may comprise 0.1 to 20%, preferably 0.5 to 15% and more preferably 1 to 10% by wt. of the composition.

The optional acyl isethionate may be an alkoxylated isethionate such as is described in Ilardi et al., U.S. Pat. No. 5,393,466, titled "Fatty Acid Esters of Polyalkoxylated isethonic acid; issued Feb. 28, 1995; hereby incorporated by reference. This compound has the general formula:

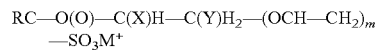
—SO$_3$M$^+$ wherein R is an alkyl group having 8 to 18 carbons, m is an integer from 1 to 4, X and Y are hydrogen or an alkyl group having 1 to 4 carbons and M$^+$ is a monovalent cation such as, for example, sodium, potassium or ammonium.

Anionic detergent surfactant(s) which may be optionally used in the invention may be $C_8$-$C_{22}$ alkyl chains of: alkyl sulfosuccinates, methyl acyl taurates, acyl sarcosinates, acyl alaninates, acyl threoninates, alkylglycerylether sulfonates, alkyl sulfates, acyl lactylates, paraffin sulfonates, linear alkyl benzene sulfonates, alpha sulfo fatty acid esters, alkyl ether carboxylates, alkyl phosphate esters, ethoxylated alkyl phosphate esters, alpha olefin sulfates, and alkyl ether sulfates and mixtures thereof. The counter ion of these surfactants is selected from, but not limited to, Na, K, NH$_4$, N(CH$_2$CH$_2$OH)$_3$.

In one form of the invention, as noted, the compositions comprise, in addition to 0.1 to 20% of individual surfactants or mixtures of $C_{10}$, $C_{12}$ and $C_{14}$ acyl glycinates and 0.1 to 20% $C_{14}$ acyl glutamate, 1 to 25%, preferably 5 to 20% and more preferably 10 to 15% by wt. of $C_8$ to $C_{24}$ fatty acid soap, preferably $C_{10}$ to $C_{20}$ fatty acid soap, more preferably $C_{12}$ to $C_{16}$ soap most preferably $C_{12}$ to $C_{14}$ fatty acid soap.

The term "soap" is used herein in its popular sense, i.e., the alkali metal or alkanol ammonium salts of aliphatic, alkanes, or alkene monocarboxylic acids. Sodium, potassium, magnesium, mono-, di- and tri-ethanol ammonium cations, or combination thereof, are the most suitable for purposes of this invention. In general, potassium soaps are used in the compositions of this invention, but up to about 75% of the soap may be potassium, magnesium or triethanolamine soaps. The soaps useful herein are well known alkali metal salts of natural or synthetic aliphatic (alkanoic or alkenoic) acids having about 8 to about 24 carbon atoms. They may be described as alkali metal carboxylates of saturated or unsaturated hydrocarbons having about 8 to about 24 carbon atoms.

The fatty acids blend is made from fatty acids that may be different fatty acids, typically fatty acids containing fatty acid moieties with chain lengths of from $C_8$ to $C_{24}$. The fatty acid blend may also contain relatively pure amounts of one or more fatty acids. Suitable fatty acids include, but are not limited to, butyric, caproic, caprylic, capric, lauric, myristic, myristelaidic, pentadecanoic, palmitic, palmitoleic, margaric, heptadecenoic, stearic, oleic, linoleic, linolenic, arachidic, gadoleic, behenic and lignoceric acids and their isomers. In a preferred embodiment, the fatty acid blend has fatty acids with fatty acids moiety chains length of 10 (capric acid) and 12 (lauric acid) carbon atoms. In preferred embodiments, the fatty acid blend has low levels of fatty acid with saturated fatty acid moiety chain length of 14 carbon atoms (myristic acid).

Amphoteric Surfactants

One or more amphoteric surfactants may optionally be used in this invention as a co-surfactant and stabilizer. Amphoteric surfactants are preferably used at levels as low as 3, 2, 1 or 0% by wt. and at levels as high as 5, 10 or 20% by wt.

Suitable amphoteric surfactants include simple betaines of formula:

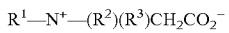

and amido betaines of formula:

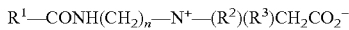

where n is 2 or 3.

In both formulae $R^1$, $R^2$ and $R^3$ are as defined previously. $R^1$ may in particular be a mixture of $C_{12}$ and $C_{14}$ alkyl groups derived from coconut oil so that at least half, preferably at least three quarters of the groups $R^1$ have 10 to 14 carbon atoms. $R^2$ and $R^3$ are preferably methyl.

A further possibility is that the amphoteric detergent is a sulphobetaine of formula:

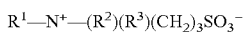

or

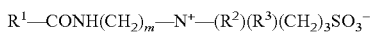

where m is 2 or 3, or variants of these in which $-(CH_2)_3SO_3^-$ is replaced by

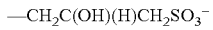

In these formulae $R^1$, $R^2$ and $R^3$ are as discussed previously.

Amphoacetates and diamphoacetates are also intended to be covered in possible zwitterionic and/or amphoteric compounds which may be used such as e.g., sodium lauroamphoacetate, sodium cocoamphoacetate, and blends thereof, and the like.

Amphoteric surfactants that are suitable include hydroxysultaines, betaines, and amphoacetates.

Nonionic Surfactants

One or more nonionic surfactants may be used in the cleansing composition of the present invention as a co-surfactant. Nonionic surfactants are preferably used at levels as low as 3, 2, 1 or 0% by wt. and at levels as high as 5, 10 or 20% by wt.

The nonionics which may be used include in particular the reaction products of compounds having a hydrophobic group and a reactive hydrogen atom, for example aliphatic alcohols, acids, amides or alkylphenols with alkylene oxides, especially ethylene oxide either alone or with propylene oxide. Specific nonionic detergent compounds are alkyl ($C_6$-$C_{22}$) phenols ethylene oxide condensates, the condensation products of aliphatic ($C_8$-$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxide, and the like.

Preferred nonionic surfactants include carboxylic acid/alcohol ethoxylates having the following structures a) HOCH2(CH2)n(CH2CH2O)x H or
b) HOOC(CH2)$_m$(CH2CH2O)y H;
where m, n are independently <18; and x, y are independently >1. preferably m, n are independently 6 to 18; x, y are independently 1 to 30;
c) HOOC(CH2)i-CH=CH—(CH2)k(CH2CH2O)z H;
where i, k are independently 5 to 15; and z is independently 5 to 50. preferably k are independently 6 to 12; and z is independently 15 to 35.

The nonionic may also include a sugar amide, such as a polysaccharide amide. Specifically, the surfactant may be one of the lactobionamides described in U.S. Pat. No. 5,389,279 to Au et al. titled "Compositions Comprising Nonionic Glycolipid Surfactants issued Feb. 14, 1995; which is hereby incorporated by reference or it may be one of the sugar amides described in U.S. Pat. No. 5,009,814 to Kelkenberg, titled "Use of N-Poly hydroxyalkyl Fatty Acid Amides as Thickening Agents for Liquid Aqueous Surfactant Systems" issued Apr. 23, 1991; hereby incorporated into the subject application by reference.

Carboxylic Acids $C_{12}$-$C_{18}$ alkyl carboxylic acids may also optionally be used. Preferably, carboxylic acid(s), such as lauric ($C_{12}$), myristic ($C_{14}$) or palmitic ($C_{16}$) acids are used alone or in combination. Advantageously the carboxylic acid(s) are used at levels as low as 2, 1 or 0% by wt. and at levels as high as 4, 5, 6, 7, 8, 9 or 10% by wt.

The carboxylic acid may be used to form liquid lamellar composition, if desired.

Structurants and Rheology Modifiers

In addition to or in place of optional normal carboxylic acids; starch, lauryl alcohol, PEG distearates, or polymeric thickeners may be used as structurants. Advantageously these structurants are used at levels as low as 3, 2, 1, 0% by wt. and at levels as high as 7, 8, 9, or 10% by wt.

Polymeric structurants that can be used include, but not limited to, acrylic acid based polymers such as the Carbomer family of polymers from Lubrizol, methyl cellulose and hydroxypropyl cellulose polymers such as Methocel family of polymers from Dow Chemical, acrylates/$C_{10}$-$C_{30}$ alkyl acrylates cross polymers, acrylates/palmeth 25 acylates copolymer, acrylates/beheneth 25 methacylates copolymer and such.

Cationic Skin Conditioning Agents

A useful component in compositions according to the invention is a cationic skin feel agent or polymer, such as for example cationic celluloses. Cationic polymers are preferably used at levels as low as about 0.1 to 2% up to levels as high as the solubility limit of the specific polymer, or preferably up to about 4 to 5% by wt., provided that the solubility limit of the particular cationic polymer or blend thereof is not exceeded.

Cationic cellulose is available from Amerchol Corp. (Edison, N.J., USA) in their Polymer JR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200.

A particularly suitable type of cationic polysaccharide polymer that can be used is a cationic guar gum derivative, such as guar hydroxypropyltrimonium chloride (Commercially available from Rhone-Poulenc in their JAGUAR trademark series). Examples are JAGUAR C13S, which has a low degree of substitution of the cationic groups and high viscosity, JAGUAR C15, having a moderate degree of substitution and a low viscosity, JAGUAR C17 (high degree of substitution, high viscosity), JAGUAR C16, which is a hydroxypropylated cationic guar derivative containing a low level of substituent groups as well as cationic quaternary ammonium groups, JAGUAR 162 which is a high transparency, medium viscosity guar having a low degree of substitution, Jaguar Optima, which has a high degree of substitution and low molecular weight, and Jaguar Excel, which has a low degree of substitution and high viscosity.

Particularly preferred cationic polymers are JAGUAR C13S, JAGUAR C15, JAGUAR C17 and JAGUAR C16 and JAGUAR C162, especially JAGUAR C13S, JAGUAR C-14/BFG, Jaguar Optima and Jaguar Excel. The JAGUAR C14 BFG material is the same molecule as JAGUAR C13, except that a glyoxal cross linker has replaced the boron. Other cationic skin feel agents known in the art may be used provided that they are compatible with the inventive formulation.

In addition, the inventive cleansing composition of the invention may include 0 to 15% by wt. optional ingredients as follows: perfumes; sequestering agents, such as tetrasodium ethylenediaminetetraacetate (EDTA), EHDP or mixtures in an amount of 0.01 to 1%, preferably 0.01 to 0.05%; and soluble coloring agents, opacifiers and the like; all of which are useful in enhancing the appearance or cosmetic properties of the product.

The compositions may further comprise antimicrobials such as caprylyl glycol, 2-hydroxy-4,2', 4' trichlorodiphenylether (DP300); preservatives such as methylisothiazolinone/methylchloroisothiazolinone (Kathon, MIT), dimethyloldimethylhydantoin/iodopropynyl butylcarbamate (Glydant XL1000), parabens, sorbic acid etc., and the like.

The compositions may also comprise coconut acyl mono- or diethanol amides as suds boosters, and strongly ionizing salts such as sodium chloride and sodium sulfate may also be used to advantage for increasing viscosity. Preferably strongly ionizing salts, otherwise known as electrolytes, will be present at less than 5, 4, 3, or 1% by wt.

Antioxidants such as, for example, butylated hydroxytoluene (BHT) and the like may be used advantageously in amounts of about 0.01% or higher if appropriate.

Emollients

The term "emollient" is defined as a substance which softens or improves the elasticity, appearance, and youthfulness of the skin (stratum corneum) by either increasing its water content, adding, or replacing lipids and other skin nutrients; or both, and keeps it soft by retarding the decrease of its water content. Preferably, a composition of the invention comprises emollients such as petrolatum, mineral oil and vegetable oils.

Moisturizers that also are humectants such as polyhydric alcohols, e.g. glycerin and propylene glycol, and the like; and polyols such as the polyethylene glycols such as Polyox WSR N-60K (PEG-45M) and the like are used in a preferred embodiment of the invention. Humectants are preferably used at a minimum of 3, 2, 1 or 0% by wt. and a maximum of 7, 8, 9 or 10% by wt.

Hydrophobic emollients with weight average particle sizes below either 1000 or 500 microns in diameter are defined herein as "finely dispersed oils" and are preferably used at a minimum of 3, 2, 1 or 0% by wt. and a maximum of 20, 30, 40 or 50% by wt.

These hydrophobic emollients include but are not limited to the following:
(a) silicone oils and modifications thereof such as linear and cyclic polydimethylsiloxanes; amino, alkyl, alkylaryl, and aryl silicone oils;
(b) fats and oils including natural fats and oils (triglycerides) such as jojoba, soybean, sunflower, safflower, algal, rice bran, avocado, almond, olive, sesame, persic, castor, coconut, mink oils; cacao fat; beef tallow, lard; hardened oils obtained by hydrogenating the aforementioned oils; and synthetic mono, di and triglycerides such as myristic acid glyceride and 2-ethylhexanoic acid glyceride;
(c) waxes such as carnauba, spermaceti, beeswax, lanolin, and derivatives thereof;
(d) hydrophobic plant extracts;
(e) hydrocarbons such as petrolatum, polybutene, liquid paraffins, microcrystalline wax, ceresin, squalene, pristan and mineral oil;
(f) higher alcohols such as lauryl, cetyl, stearyl, oleyl, behenyl, cholesterol and 2-hexydecanol alcohol;
(g) esters such as cetyl octanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate;
(h) essential oils and extracts thereof such as mentha, jasmine, camphor, white cedar, bitter orange peel, ryu, turpentine, cinnamon, bergamot, citrus unshiu, calamus, pine, lavender, bay, clove, hiba, *eucalyptus*, lemon, starflower, thyme, peppermint, rose, sage, sesame, ginger, basil, juniper, lemon grass, rosemary, rosewood, avocado, grape, grapeseed, myrrh, cucumber, watercress, calendula, elder flower, geranium, linden blossom, amaranth, seaweed, ginko, *ginseng*, carrot, guarana, tea tree, jojoba, comfrey, oatmeal, cocoa, neroli, vanilla, green tea, penny royal, aloe vera, menthol, cineole, eugenol, citral, citronelle, borneol, linalool, geraniol, evening primrose, camphor, thymol, spirantol, penene, limonene and terpenoid oils;
(i) mixtures of any of the foregoing components, and the like.

Optional Active Agents

Advantageously, active agents other than conditioning agents such as emollients or moisturizers defined above may be added to the cleansing composition in a safe and effective amount during formulation to treat the skin during the use of the product. Suitable active ingredients include those that are water soluble or are dispersible within the limits provided above. Suitable active agents may be advantageously selected from antimicrobial and antifungal actives, vitamins, anti-acne actives; anti-wrinkle, anti-skin atrophy and skin repair actives; skin barrier repair actives; non-steroidal cosmetic soothing actives; artificial tanning agents and accelerators; skin lightening actives; sunscreen actives; sebum stimulators; sebum inhibitors; anti-oxidants; protease inhibitors; skin tightening agents; anti-itch ingredients; hair growth inhibitors; 5-alpha reductase inhibitors; desquamating enzyme enhancers; anti-glycation agents; topical anesthetics, or mixtures thereof; and the like.

These active agents may be selected from water soluble active agents, oil soluble active agents, pharmaceutically-acceptable salts and mixtures thereof. Advantageously the agents will be soluble or dispersible in the cleansing composition. The term "active agent" as used herein, means personal care actives which can be used to deliver a benefit to the skin and/or hair and which generally are not used to confer a conditioning benefit, as is conferred by humectants and emollients previously described herein. The term "safe and effective amount" as used herein, means an amount of active agent high enough to modify the condition to be treated or to deliver the desired skin care benefit, but low enough to avoid serious side effects. The term "benefit," as used herein, means the therapeutic, prophylactic, and/or chronic benefits associated with treating a particular condition with one or more of the active agents described herein. What is a safe and effective amount of the active agent ingredient will vary with the specific active agent, the ability of the active to penetrate through the skin, the age, health condition, and skin condition of the user, and other like factors. Preferably the composition of the present invention comprise from about 0.01% to about 50%, more preferably from about 0.05% to about 25%, even more preferably 0.1% to about 10%, and most preferably 0.1% % to about 5%, by weight of the active agent component Anti-acne actives can be effective in treating acne vulgaris, a chronic disorder of the pilosebaceous follicles. Non-limiting examples of useful anti-acne actives include the keratolytics such as salicylic acid (o-hydroxybenzoic acid), derivatives of salicylic acid such as 5-octanoyl salicylic acid and 4 methoxysalicylic acid, and resorcinol; retinoids such as retinoic acid and its derivatives (e.g., cis and trans); sulfur-containing D and L amino acids and their derivatives and salts, particularly their N-acetyl derivatives, mixtures thereof and the like.

Antimicrobial and antifungal actives can be effective to prevent the proliferation and growth of bacteria and fungi. Non-limiting examples of antimicrobial and antifungal actives include b-lactam drugs, quinolone drugs, ciprofloxacin, norfloxacin, tetracycline, erythromycin, amikacin, 2,4, 4'-trichloro-2'-hydroxy diphenyl ether, 3,4,4'-trichlorobanilide, phenoxyethanol, triclosan; triclocarban; and mixtures thereof and the like.

Anti-wrinkle, anti-skin atrophy and skin repair actives can be effective in replenishing or rejuvenating the epidermal layer. These actives generally provide these desirable skin care benefits by promoting or maintaining the natural process of desquamation. Non-limiting examples of anti-wrinkle and anti-skin atrophy actives include vitamins, minerals, and skin nutrients such as milk, vitamins A, E, and K; vitamin alkyl esters, including vitamin C alkyl esters; magnesium, calcium, copper, zinc and other metallic components; retinoic acid and its derivatives (e.g., cis and trans); retinal; retinol; retinyl esters such as retinyl acetate, retinyl palmitate, and retinyl propionate; vitamin B 3 compounds (such as niacinamide and nicotinic acid), alpha hydroxy acids, beta hydroxy acids, e.g. salicylic acid and derivatives thereof (such as 5-octanoyl salicylic acid, heptyloxy 4 salicylic acid, and 4-methoxy salicylic acid); mixtures thereof and the like.

Skin barrier repair actives are those skin care actives which can help repair and replenish the natural moisture barrier function of the epidermis. Non-limiting examples of skin barrier repair actives include lipids such as cholesterol, ceramides, sucrose esters, stearic acid and pseudo-ceramides as described in European Patent Specification No. 556,957; ascorbic acid; biotin; biotin esters; phospholipids, mixtures thereof, and the like.

Non-steroidal cosmetic soothing actives can be effective in preventing or treating inflammation of the skin. The soothing active enhances the skin appearance benefits of the present invention, e.g., such agents contribute to a more uniform and acceptable skin tone or color. Non-limiting examples of cosmetic soothing agents include the following categories: propionic acid derivatives; acetic acid derivatives; fenamic acid derivatives;

mixtures thereof and the like. Many of these cosmetic soothing actives are described in U.S. Pat. No. 4,985,459 to Sunshine et al., issued Jan. 15, 1991, incorporated by reference herein in its entirety.

Artificial tanning actives can help in simulating a natural suntan by increasing melanin in the skin or by producing the appearance of increased melanin in the skin. Non-limiting examples of artificial tanning agents and accelerators include dihydroxyacetone; tyrosine; tyrosine esters such as ethyl tyrosinate and glucose tyrosinate; mixtures thereof, and the like.

Skin lightening actives can actually decrease the amount of melanin in the skin or provide such an effect by other mechanisms. Non-limiting examples of skin lightening actives useful herein include aloe extract, alpha-glyceryl-L-ascorbic acid, aminotyroxine, ammonium lactate, glycolic acid, hydroquinone, 4 hydroxyanisole, mixtures thereof, and the like.

Also useful herein are sunscreen actives. A wide variety of sunscreen agents are described in U.S. Pat. No. 5,087,445, to Haffey et al., issued Feb. 11, 1992; U.S. Pat. No. 5,073,372, to Turner et al., issued Dec. 17, 1991; U.S. Pat. No. 5,073,371, to Turner et al. issued Dec. 17, 1991; and Segarin, et al., at Chapter VIII, pages 189 et seq., of Cosmetics Science and Technology, all of which are incorporated herein by reference in their entirety. Non-limiting examples of sunscreens which are useful in the compositions of the present invention are those selected from the group consisting of octyl methoxyl cinnamate (Parsol MCX) and butyl methoxy benzoylmethane (Parsol 1789), 2-ethylhexyl p-methoxycinnamate, 2-ethylhexyl N,N-dimethyl-p-aminobenzoate, p-aminobenzoic acid, 2-phenylbenzimidazole-5-sulfonic acid, oxybenzone, mixtures thereof, and the like.

Sebum stimulators can increase the production of sebum by the sebaceous glands. Non-limiting examples of sebum stimulating actives include bryonolic acid, dehydroetiandrosterone (DHEA), orizanol, mixtures thereof, and the like.

Sebum inhibitors can decrease the production of sebum by the sebaceous glands. Non-limiting examples of useful sebum inhibiting actives include aluminum hydroxy chloride, corticosteroids, dehydroacetic acid and its salts, dichlorophenyl imidazoldioxolan (available from Elubiol), mixtures thereof, and the like.

Also useful as actives in the present invention are protease inhibitors. Protease inhibitors can be divided into two general classes: the proteinases and the peptidases. Proteinases act on specific interior peptide bonds of proteins and peptidases act on peptide bonds adjacent to a free amino or carboxyl group on the end of a protein and thus cleave the protein from the outside. The protease inhibitors suitable for use in the present invention include, but are not limited to, proteinases such as serine proteases, metalloproteases, cysteine proteases, and aspartyl protease, and peptidases, such as carboxypepidases, dipeptidases and aminopepidases, mixtures thereof and the like.

Other useful as active ingredients in the present invention are skin tightening agents. Non-limiting examples of skin tightening agents which are useful in the compositions of the present invention include monomers which can bind a polymer to the skin such as terpolymers of vinylpyrrolidone, methacrylic acid and a hydrophobic monomer comprised of long chain alkyl (meth)acrylates, mixtures thereof, and the like.

Active ingredients in the present invention may also include anti-itch ingredients. Suitable examples of anti-itch ingredients which are useful in the compositions of the present invention include hydrocortisone, methdilizine and trimeprazineare, mixtures thereof, and the like.

Non-limiting examples of hair growth inhibitors which are useful in the compositions of the present invention include 17 beta estradiol, anti angiogenic steroids, *curcuma* extract, cycloxygenase inhibitors, evening primrose oil, linoleic acid and the like. Suitable 5-alpha reductase inhibitors such as ethynylestradiol and, genistine mixtures thereof, and the like.

Non-limiting examples of desquamating enzyme enhancers which are useful in the compositions of the present invention include alanine, aspartic acid, N methyl serine, serine, trimethyl glycine, mixtures thereof, and the like.

A non-limiting example of an anti-glycation agent which is useful in the compositions of the present invention would be Amadorine (available from Barnet Products Distributor), and the like.

Solid Particulate Optical Modifiers

An useful optional component of compositions according to the present invention is that of solid particulate optical modifiers, preferably light reflecting platelet shaped or platy particles. These particles will preferably have an average particle size D50 ranging from about 25,000 to about 150,000 nm. For plate-like materials the average particle size is a number average value. The platelets are assumed to have a circular shape with the diameter of the circular surface averaged over many particles. The thickness of the plate-like particles is considered to be a separate parameter. For instance, the platelets can have an average particle size of 35,000 nm and an average thickness of 400 nm. For purposes herein, thickness is considered to range from about 100 to about 600 nm. Laser light scattering can be utilized for measurement except that light scattered data has to be mathematically corrected from the spherical to the non-spherical shape. Optical and electron microscopy may be used to determine average particle size. Thickness is normally only determined via optical or electron microscopy.

The refractive index of these particles may be at least about 1.8, generally from about 1.9 to about 4, e.g. from about 2 to about 3, and between about 2.5 and 2.8.

Illustrative but not limiting examples of light reflecting particles are bismuth oxychloride (single crystal platelets) and titanium dioxide and/or iron oxide coated mica. Suitable bismuth oxychloride crystals are available from EM Industries, Inc. under the trademarks Biron® NLY-L-2X CO and Biron® Silver CO (wherein the platelets are dispersed in castor oil); Biron® Liquid Silver (wherein the particles are dispersed in a stearate ester); and Nailsyn® IGO, Nailsyn® II C2X and Nailsyn® II Platinum 25 (wherein the platelets are dispersed in nitrocellulose). Most preferred is a system where bismuth oxychloride is dispersed in a $C_2$—$C_{40}$ alkyl ester such as in Biron® Liquid Silver.

Among the suitable titanium dioxide coated mica platelets are materials available from EM Industries, Inc. These include Timiron® MP-45 (particle size range 49,000-57,000 nm), Timiron® MP-99 (particle size range 47,000-57,000 nm), Timiron® MP-47 (particle size range 28,000-38,000 nm), Timiron® MP-149 (particle size range 65,000-82,000 nm), and Timiron® MP-18 (particle size range 41,000-51,000 nm). The weight ratio of titanium dioxide coating to the mica platelet may range from about 1:10 to about 5:1, preferably from about 1:6 to about 1:7, by weight. Advantageously the compositions will generally be substantially free of titanium dioxide outside of that required for coating mica.

Among the suitable iron oxide and titanium dioxide coated mica platelets are materials available from EM Industries, Inc. These include Timiron® MP-28 (particle size range 27,000-37,000 nm), Timiron® MP-29 (particle size range 47,000-55,000 nm), and Timiron® MP-24 (particle size range 56,000-70,000 nm).

Among the suitable iron oxide coated mica platelets are materials available from EM Industries, Inc. These include Colorona® Bronze Sparkle (particle size range 28,000-42,000 nm), Colorona® Glitter Bronze (particle size range 65,000-82,000 nm), Colorona® Copper Sparkle (particle size range 25,000-39,000 nm), and Colorona® Glitter Copper (particle size range 65,000-82,000 nm).

Suitable coatings for mica other than titanium dioxide and iron oxide may also achieve the appropriate optical properties required for the present invention. These types of coated micas must also meet the refractive index of at least about 1.8. Other coatings include silica on the mica platelets.

Exfoliants

The inventive composition may contain particles that are greater than 50 microns in average diameter that help remove dry skin. Not being bound by theory, the degree of exfoliation depends on the size and morphology of the particles. Large and rough particles are usually very harsh and irritating. Very small particles may not serve as effective exfoliants. Such exfoliants used in the art include natural minerals such as silica, talc, calcite, pumice, tricalcium phosphate; seeds such as rice, apricot seeds, etc.; crushed shells such as almond and walnut shells; oatmeal; polymers such as polyethylene and polypropylene beads, flower petals and leaves; microcrystalline wax beads, synthetic wax beads, jojoba ester beads, and the like. These exfoliants come in a variety of particle sizes and morphology ranging from micron sized to a few mm. They also have a range of hardness. Some examples are given in table B below.

TABLE B

| Material | Hardness (Mohs) |
| --- | --- |
| Talc | 1 |
| Calcite | 3 |
| Pumice | 4-6 |
| Walnut Shells | 3-4 |
| Dolomite | 4 |
| Polyethylene | ~1 |

The invention will now be described in greater detail by way of the following non-limiting examples. The examples are for illustrative purposes only and not intended to limit the invention in any way. Physical test methods are described below:

Except in the operating and comparative examples, or where otherwise explicitly indicated, all numbers in this description indicating amounts or ratios of materials or conditions or reaction, physical properties of materials and/or use are to be understood as modified by the word "about".

Where used in the specification, the term "comprising" is intended to include the presence of stated features, integers, steps, components, but not to preclude the presence or addition of one or more features, integers, steps, components or groups thereof.

All percentages in the specification and examples are intended to be by weight unless stated otherwise.

Several inventive and comparative compositions were prepared according to Tables 1 to 7 and the lather production, lather texture, stearic acid replenishment, skin mildness properties, were measured for selected examples according to the methods provided below. Methods of preparation of the examples are provided below.

Methods to Prepare the Examples:

Syndet ("Synthetic Detergent") Batch Process
1. Add water to main beaker
2. Premelt fatty acids and EGDS in side phase
3. Add tetrasodium EDTA, begin to heat
4. Add lauroamphoacetate at 50 C
5. Add acyl glycinate at 50 C
6. Premix methocel (thickener) and glycerin and add to batch at 60 C and mix for 5-10 min 7. Add fatty acids and EGDS mix at 70-75 till homogeneous (10-15 min)
8. Add acyl glutamate at 65 C and mix until homogenous (15 min); keep temp between 60-70 C
9. Add Neolone (preservative) under 40 C
10. Add potassium hydroxide
11. Add fragrance to the batch
12. pH adjust (between 6.5 and 7.1)

Soap-Syndet Batch Process (for Inventive Formulations Containing Glycinate/Glutamate)

1. Add water to main beaker
2. Premelt fatty acids and EGDS in side phase
3. Add tetrasodium EDTA, begin to heat
4. Premix guar and propylene glycol and add to batch, mix for 5-10 min
5. Premix methocel (thickener) and glycerin and add to batch at 60 C and mix for 5-10 min
6. Add fatty acids and EGDS mix at 80 till homogeneous (10-15 min)
7. Add potassium hydroxide and mix for 30 min. Hold temp at 80-85 C
8. Begin to cool
9. Add acyl glycinate at 70 C
10. Add acyl glutamate at 65 C and mix until homogenous (15 min); keep temp between 60-70 C
11. Add cocoamidopropyl betaine below 55 C
12. Add Neolone (preservative) under 40 C
13. Add fragrance to the batch Soap-Syndet Batch Process (for Non-Inventive Formulations Containing SLES)

1. Add water to main beaker
2. Premelt fatty acids and EGDS in side phase
3. Add tetrasodium EDTA, begin to heat
4. Premix guar and propylene glycol and add to batch, mix for 5-10 min
5. Premix methocel (thickener) and glycerin and add to batch at 60 C and mix for 5-10 min
6. Add fatty acids and EGDS mix at 80 till homogeneous (10-15 min)
7. Add potassium hydroxide and mix for 30 min. Hold temp at 80-85 C
8. Add SLES, mix until fully dissolved. Begin to cool.
9. Add cocoamidopropyl betaine below 55 C
10. Add Neolone (preservative) under 40 C
11. Add fragrance to the batch Test Methods:
Lather Volume Test:
Equipment: SITA Lab Solutions—Sita Foam Tester R-2000
Standard Measurement Parameters:
Mixing Speed: 1000 rpm
Measurement time (Single time point): 15 Seconds
Dilution: 250 mL
Sample Size: 10 g
Procedure:
1) Run one cleaning cycle using hot tap water, in order to ensure vessel is clean, and to equilibrate temperature of vessel.
2) Fill Water Reservoir (Clear vessel on back of machine) with 38 C tap water. Ensure that water in vessel remains at 38 C+/−0.5 C for each measurement.
3) Weigh 10.0 g of product to be tested in a 10 mL syringe
4) Inject product to be tested into bottom of main vessel, being careful not to hit vessel walls or metal shaft in middle.
5) Check measurement parameters and enter in parameters defined above.
6) Begin measurement, record results Lather Texture Test for Syndet Formulations:
Equipment: TA XT plus Texture Analyzer with Texture Exponent 32 Software (With Mesh Screen)
Standard Measurement Parameters:
Sample Size: 5 g
Dilution: 195 g
Program Settings:
Test Mode: Compression
Pre-Test Speed: 10 mm/sec
Test Speed: 0.5 mm/sec
Post-Test Speed: 2 mm/sec
Testing Mode: Distance
Distance: 4 mm
Hold Time: 0.01 sec
Trigger Type: Auto (Force)
Trigger Force: 0.005 kg
Advanced Options: Off
Lather generation Procedure:
1) Dilute sample to 2.5% (5 g product and 195 g of hot tap water ~37 deg C.)
2) Pour dilution into pump & mesh bottle
3) Pump dilution through mesh into glass cylinder to the top. (Ensure there are no air bubbles). Use spatula to level the foam at top of the cylinder
4) Place cylinder onto texture analyzer holder.
5) Check measurement parameters and enter in parameters defined above.
6) Begin measurement, record results Lather Texture Test for Soap Syndet formulations:
Equipment: TA XT plus Texture Analyzer with Texture Exponent 32 Software (With Implement)
Standard Measurement Parameters:
Sample Size: 1.5 g
Dilution: 8.5 g
Program Settings:
Test Mode: Compression
Pre-Test Speed: 10 mm/sec
Test Speed: 0.5 mm/sec
Post-Test Speed: 2 mm/sec
Testing Mode: Distance
Distance: 4 mm
Hold Time: 0.01 sec
Trigger Type: Auto (Force)
Trigger Force: 0.005 kg
Advanced Options: Off
Lather generation Procedure:
1) Wet and ring out implement with hot tap water
2) Using a syringe, add 1.5 g of product onto implement
3) Add additional 8.5 g of water onto the implement with syringe to dilute product
4) Generate lather using implement and gloved hands.
5) Scoop lather into cylinder. (Ensure there are no air bubbles). Use spatula to level the foam at top of the cylinder
6) Place cylinder onto texture analyzer holder.
7) Check measurement parameters and enter in parameters defined above.
8) Begin measurement, record results Stearic Acid Replenishment Test:
Skin lipids: Ceramides, Cholesterol, Fatty Acids (C20,24,26, etc.)
Substrate: A model system (filter papers) consists these 3 categories of skin lipids+lipid dye
Procedure:
1) Dissolve lipids+dyes in a solution;
2) Deposit the solution on the filter paper;
3) Heat at 70 C to form bilayer;

4) Put "lipid paper" in the test sample solutions (about 10% dilution);
5) Vacuum dry washed "lipid paper" and dissolve into solvent (chloroform+methanol);
6) Assess the remaining lipid using a flurometer.

Protein Damage Test
Standard Measurement Parameters:
Balance, analytical
Beakers, 100 mL
Stir bars, medium
Stir plate
Syringe, 10 mL
Scintillation vials, 20 mL
Conventional oven, set at 75° C.
DI water
Procedure:
1. Weigh 6.25 g of product into a 100-mL beaker and dilute it to 50 g with DI water.
2. Mix the solution on a stir plate @ 300 rpm (set dial at 4 on stirring plate) until the solution looks uniform or the entire sample is dissolved.
3. Record the pH of the solution.
4. Withdraw 6 mL of solution using a syringe.
5. Filter solution through a 0.45-micron syringe filter onto a scintillation vial.
6. Cap the vial and label it as blank. A blank is needed to correct for any soluble material.
7. Add 2 g of Zein to the remaining solution and equilibrate for 1 hour at constant stirring speed (300 rpm). After 10 minutes of stirring, if all or most of the Zein dissolved, add an additional 1 g of Zein. Keep adding more Zein in 1 g increments every 5-10 minutes until there is undissolved Zein floating in the solution.
8. After 1 hour of constant stirring, allow solution to settle for 5 minutes.
9. Withdraw 6 mL of the supernatant solution using a syringe and filter it through a 0.45 micron syringe filter onto a scintillation vial.
10. Cap the vial and label it as sample.
11. Perform nonvolatiles on both samples using a conventional oven set at 75° C. Allow samples to dry overnight.
12. Calculate the percent Zein dissolved.

The invention is exemplified by several examples listed in the Tables below:

Typical synthetic cleansing formulations in the US and Japanese markets are Caress® marketed by Unilever US and Biore® marketed Kao corporation Japan. The lather volume of Caress® body wash is about 370 ml and the texture is 8.5 grams, more volume less quality. The respective values for Biore are 270 ml and 16.9 grams, less volume but slightly more quality. In examples exemplified in Table 1 (inventive formulations) all the formulations exhibit a volume of over 300 ml and a texture of above 20 grams. These indicate that these formulations produce as much volume (lather volume) as typical syndet formulations but much higher texture (foam quality). Almost all these formulations contain $C_{14}$ acyl glutamate and only one contains $C_{12}$ acyl glutamate. However, the one formulation with $C_{12}$ glutamate, different from formulations in Table 2 discussed below, is in a very specific area where ratio of $C_{12}$ acyl glutamate to $C_{12}$ acyl glycinate is in a narrow range of about 0.35 to 0.45. Above this range, the compositions are not optimal as defined by foam volume and texture, and below this range, the compositions are paste-like.

The formulations listed in Table 2 (non-inventive formulations) produce lather volume over 300 ml but the texture (foam quality) is below 18 grams which is typical of regular syndet formulations. Most of these formulations contain $C_{12}$ acyl glutamate and four formulations contain $C_{14}$ acyl glutamate and these are $C_{14}$ acyl glutamate and $C_{10}$ acyl glycinate at a ratio of 0.55 (F) and $C_{14}$ acyl glutamate and $C_{14}$ acyl glycinate at ratios of 0.41 (I), 7.57 (H) and 12.05 (G).

The formulations listed in Table 3 (non-inventive formulations) produce a lather texture of over 20 grams but the lather volume falls short of 300 ml. There is only one formulation in this table that contain $C_{14}$ acyl glutamate and $C_{12}$ acyl glycinate and this is at a ratio of 4.02 (K), above our claimed limitation.

The formulations listed in Table 4 (non-inventive formulations) produce lather volume less than 300 ml and texture less than 18 grams i.e., these are somewhat inferior to even typical syndet bodywashes. In this table there are four formulations that contain $C_{14}$ acyl glutamate, two with $C_{10}$ acyl glycinate at ratios of 13.34 (N) and 28.11 (M) and two with $C_{12}$ acyl glycinate at ratios of 12.05 (T) and 25.44 (S).

From the above tables, it can be seen that in order to obtain defined advantage in both lather volume and lather texture (defined by applicants as volume of greater than 300 ml as measured by lather test defined in protocol; and texture of greater than 20 grams, as also defined in protocol), it is critical that $C_{14}$ glutamate be combined with $C_{10}$ glycinate, $C_{12}$ glycinate, $C_{14}$ glycinate or mixtures thereof in defined ratios.

Table 2, Table 3 and Table 4 clearly show that $C_{12}$ glutamate will not provide this benefit. Further, from Comparative Examples, it can be seen that even when $C_{14}$ glutamate is used, the ratio of $C_{14}$ acyl glutamate to $C_{10}$ acyl glycinate (F, M and N), or $C_{14}$ acyl glutamate to $C_{12}$ acyl glycinate (K, S and T) or $C_{14}$ acyl glutamate to $C_{14}$ acyl glycinate (G, H, I and L) must be within certain defined limits.

Syndet (Synthetic Detergent) Formulations

TABLE 1

Syndet Formulations with Lather Volume @ 15 sec >300 mL and Lather Texture >20 g - Inventive compositions

| | Syndet Prototype | | | | | | |
|---|---|---|---|---|---|---|---|
| | 1 % Active | 2 % Active | 3 % Active | 4 % Active | 5 % Active | 6 % Active | 7 % Active |
| DI Water | 70.644 | 68.354 | 69.047 | 70.432 | 71.817 | 68.052 | 68.939 |
| Tetrasodium EDTA | 0.05 | 0.05 | 0.05 | 0.05 | 0.05 | 0.05 | 0.05 |
| Sodium Lauroamphoacetate | 3.36 | 3.36 | 3.36 | 3.36 | 3.36 | 3.36 | 3.36 |
| Methylcellulose | 0.5 | 0.5 | 0.5 | 0.5 | 0.5 | 0.5 | 0.5 |
| Glycerin (Porcine-Free) | 4 | 4 | 4 | 4 | 4 | 4 | 4 |
| Lauric Acid | 1.42 | 1.42 | 1.42 | 1.42 | 1.42 | 1.42 | 1.42 |
| Myristic Acid | 1.96 | 1.96 | 1.96 | 1.96 | 1.96 | 1.96 | 1.96 |
| Stearic Acid | 0.54 | 0.54 | 0.54 | 0.54 | 0.54 | 0.54 | 0.54 |

TABLE 1-continued

Syndet Formulations with Lather Volume @ 15 sec >300 mL and Lather Texture >20 g - Inventive compositions

| | | | | | | | |
|---|---|---|---|---|---|---|---|
| EGDS | 0.5 | 0.5 | 0.5 | 0.5 | 0.5 | 0.5 | 0.5 |
| $C_{10}$ acyl glycinate | | 3.183 | 4.245 | 6.367 | 8.489 | | |
| $C_{12}$ acyl glycinate | 11.789 | | | | | 5.239 | 7.859 |
| $C_{14}$ acyl glycinate | | | | | | | |
| $C_{12}$ acyl glutamate | 4.888 | | | | | | |
| $C_{14}$ acyl glutamate | | 15.784 | 14.03 | 10.522 | 7.015 | 14.030 | 10.522 |
| Acyl glutamate/acyl glycinate ratio | 0.41 | 4.96 | 3.3 | 1.65 | 0.83 | 2.68 | 1.34 |
| MIT | 0.0091 | 0.0091 | 0.0091 | 0.0091 | 0.0091 | 0.0091 | 0.0091 |
| Potassium Hydroxide | 0.09 | 0.09 | 0.09 | 0.09 | 0.09 | 0.09 | 0.09 |
| Fragrance | 0.25 | 0.25 | 0.25 | 0.25 | 0.25 | 0.25 | 0.25 |
| pH Adjust to 6.5-7.1 w/ Citric Acid or Potassium Hydroxide | | | | | | | |
| Lather Volume, ml | 423 | 323 | 330 | 302 | 398 | 325 | 339 |
| Lather Texture, grams | 20.9 | 20.5 | 20.3 | 21 | 21 | 20.2 | 22.2 |

| | Syndet Prototype | | | | | |
|---|---|---|---|---|---|---|
| | 8 % Active | 9 % Active | 10 % Active | 11 % Active | 12 % Active | 13 % Active |
| DI Water | 69.828 | 70.271 | 71.27 | 67.235 | 67.554 | 68.193 |
| Tetrasodium EDTA | 0.05 | 0.05 | 0.05 | 0.05 | 0.05 | 0.05 |
| Sodium Lauroamphoacetate | 3.36 | 3.36 | 3.36 | 3.36 | 3.36 | 3.36 |
| Methycellulose | 0.5 | 0.5 | 0.5 | 0.5 | 0.5 | 0.5 |
| Glycerin (Porcine-Free) | 4 | 4 | 4 | 4 | 4 | 4 |
| Lauric Acid | 1.42 | 1.42 | 1.42 | 1.42 | 1.42 | 1.42 |
| Myristic Acid | 1.96 | 1.96 | 1.96 | 1.96 | 1.96 | 1.96 |
| Stearic Acid | 0.54 | 0.54 | 0.54 | 0.54 | 0.54 | 0.54 |
| EGDS | 0.5 | 0.5 | 0.5 | 0.5 | 0.5 | 0.5 |
| $C_{10}$ acyl glycinate | | | | | | |
| $C_{12}$ acyl glycinate | 10.479 | 11.789 | 14.93 | | | |
| $C_{14}$ acyl glycinate | | | | 4.303 | 5.737 | 8.605 |
| $C_{12}$ acyl glutamate | | | | | | |
| $C_{14}$ acyl glutamate | 7.014 | 5.261 | 1.05 | 15.784 | 14.03 | 10.522 |
| Acyl glutamate/acyl glycinate ratio | 0.67 | 0.44 | 0.07 | 3.67 | 2.45 | 1.22 |
| MIT | 0.0091 | 0.0091 | 0.0091 | 0.0091 | 0.0091 | 0.0091 |
| Potassium Hydroxide | 0.09 | 0.09 | 0.09 | 0.09 | 0.09 | 0.09 |
| Fragrance | 0.25 | 0.25 | 0.25 | 0.25 | 0.25 | 0.25 |
| pH Adjust to 6.5-7.1 w/ Citric Acid or Potassium Hydroxide | | | | | | |
| Lather Volume, ml | 334 | 384 | 354 | 392 | 391 | 396 |
| Lather Texture, grams | 23.4 | 23.9 | 21.8 | 23.4 | 25.5 | 22.7 |

TABLE 2

Syndet Formulations with Lather Volume @ 15 sec >300 mL and Lather Texture <20 g - Non-inventive compositions

| | Syndet Prototype | | | | | | | | |
|---|---|---|---|---|---|---|---|---|---|
| | Comp A % Active | Comp B % Active | Comp C % Active | Comp D % Active | Comp E % Active | Comp F % Active | Comp G % Active | Comp H % Active | Comp I % Active |
| DI Water | 68.727 | 69.047 | 69.686 | 70.325 | 69.525 | 72.510 | 66.8109 | 72.5609 | 69.151 |
| Tetrasodium EDTA | 0.05 | 0.05 | 0.05 | 0.05 | 0.05 | 0.05 | 0.05 | 0.05 | 0.05 |
| Sodium Lauroamphoacetate | 3.36 | 3.36 | 3.36 | 3.36 | 3.36 | 3.36 | 3.36 | 3.36 | 3.36 |
| Methycellulose | 0.5 | 0.5 | 0.5 | 0.5 | 0.5 | 0.5 | 0.5 | 0.5 | 0.5 |
| Glycerin (Porcine-Free) | 4 | 4 | 4 | 4 | 4 | 4 | 4 | 4 | 4 |
| Lauric Acid | 1.42 | 1.42 | 1.42 | 1.42 | 1.42 | 1.42 | 1.42 | 1.42 | 1.42 |
| Myristic Acid | 1.96 | 1.96 | 1.96 | 1.96 | 1.96 | 1.96 | 1.96 | 1.96 | 1.96 |
| Stearic Acid | 0.54 | 0.54 | 0.54 | 0.54 | 0.54 | 0.54 | 0.54 | 0.54 | 0.54 |
| EGDS | 0.5 | 0.5 | 0.5 | 0.5 | 0.5 | 0.5 | 0.5 | 0.5 | 0.5 |
| $C_{10}$ acyl glycinate | | | | | | 9.550 | | | |
| $C_{12}$ acyl Glycinate | 3.930 | 5.239 | 7.859 | 10.479 | | | | | |
| $C_{14}$ acyl glycinate | | | | | 12.908 | | 1.57 | 1.72 | 12.908 |
| $C_{12}$ acyl Glutamate | 14.664 | 13.035 | 9.776 | 6.517 | 4.888 | | | | |
| $C_{14}$ acyl glutamate | | | | | | 5.260 | 18.94 | 13.04 | 5.261 |
| Acyl glutamate/acyl glycinate ratio | 3.73 | 2.49 | 1.24 | 0.62 | 0.38 | 0.55 | 12.05 | 7.57 | 0.41 |
| MIT | 0.0091 | 0.0091 | 0.0091 | 0.0091 | 0.0091 | 0.0091 | 0.0091 | 0.0091 | 0.0091 |
| Potassium Hydroxide | 0.09 | 0.09 | 0.09 | 0.09 | 0.09 | 0.09 | 0.09 | 0.09 | 0.09 |
| Fragrance | 0.25 | 0.25 | 0.25 | 0.25 | 0.25 | 0.25 | 0.25 | 0.25 | 0.25 |
| pH Adjust to 6.5-7.1 w/ Citric Acid or Potassium Hydroxide | | | | | | | | | |
| Lather Volume, ml | 333 | 321 | 344 | 435 | 236 | 302 | 309 | 305 | 314 |
| Lather Texture, grams | 16.1 | 17.1 | 16.3 | 16.9 | 16.3 | 17.3 | 17.9 | 18.9 | 16.9 |

TABLE 3

Syndet Formuations with Lather Volume @ 15 sec <300 mL and Lather Texture >20 g - Non-inventive compositions

| | Syndet Prototype | | |
|---|---|---|---|
| | Comp J % Active | Comp K % Active | Comp L % Active |
| DI Water | 68.549 | 67.61 | 68.832 |
| Tetrasodium EDTA | 0.05 | 0.05 | 0.05 |
| Sodium Lauroamphoacetate | 3.36 | 3.36 | 3.36 |
| Methycellulose | 0.5 | 0.5 | 0.5 |
| Glycerin (Porcine-Free) | 4 | 4 | 4 |
| Lauric Acid | 1.42 | 1.42 | 1.42 |
| Myristic Acid | 1.96 | 1.96 | 1.96 |
| Stearic Acid | 0.54 | 0.54 | 0.54 |
| EGDS | 0.5 | 0.5 | 0.5 |
| $C_{10}$ acyl glycinate | | | |
| $C_{12}$ acyl glycinate | | 3.93 | |
| $C_{14}$ acyl glycinate | 5.737 | | 11.474 |
| $C_{12}$ acyl glutamate | 13.035 | | |
| $C_{14}$ acyl glutamate | | 15.781 | 7.015 |
| Acyl glutamate/acyl glycinate ratio | 2.27 | 4.02 | 0.611 |
| MIT | 0.0091 | 0.0091 | 0.0091 |
| Potassium Hydroxide | 0.09 | 0.09 | 0.09 |
| Fragrance | 0.25 | 0.25 | 0.25 |
| pH Adjust to 6.5-7.1 w/ Citric Acid or Potassium Hydroxide | | | |
| Lather Volume, ml | 274 | 279 | 285 |
| Lather Texture, grams | 21.9 | 24 | 24.9 |

TABLE 4

Syndet Prototypes with Lather Volume @ 15 sec <300 mL and Lather Texture <20 g - Non-inventive compositions

| | Syndet Formulations | | | | | |
|---|---|---|---|---|---|---|
| | Comp M % Active | Comp N % Active | Comp O % Active | Comp P % Active | Comp Q % Active | Comp R % Active |
| DI Water | 66.6199 | 66.9609 | 71.178 | 72.314 | 72.883 | 68.354 |
| Tetrasodium EDTA | 0.05 | 0.05 | 0.05 | 0.05 | 0.05 | 0.05 |
| Sodium Lauroamphoacetate | 3.36 | 3.36 | 3.36 | 3.36 | 3.36 | 3.36 |
| Methycellulose | 0.5 | 0.5 | 0.5 | 0.5 | 0.5 | 0.5 |
| Glycerin (Porcine-Free) | 4 | 4 | 4 | 4 | 4 | 4 |
| Lauric Acid | 1.42 | 1.42 | 1.42 | 1.42 | 1.42 | 1.42 |
| Myristic Acid | 1.96 | 1.96 | 1.96 | 1.96 | 1.96 | 1.96 |
| Stearic Acid | 0.54 | 0.54 | 0.54 | 0.54 | 0.54 | 0.54 |
| EGDS | 0.5 | 0.5 | 0.5 | 0.5 | 0.5 | 0.5 |
| $C_{10}$ acyl glycinate | 0.711 | 1.42 | 6.367 | 8.489 | 9.550 | |
| $C_{12}$ acyl glycinate | | | | | | |
| $C_{14}$ acyl glycinate | | | | | | 4.303 |
| $C_{12}$ acyl glutamate | | | 9.776 | 6.517 | 4.888 | 14.664 |
| $C_{14}$ acyl glutamate | 19.99 | 18.94 | | | | |
| Acyl glutamate/acyl glycinate ratio | 28.11 | 13.34 | 1.54 | 0.77 | 0.51 | 3.40 |
| MIT | 0.0091 | 0.0091 | 0.0091 | 0.0091 | 0.0091 | 0.0091 |
| Potassium Hydroxide | 0.09 | 0.09 | 0.09 | 0.09 | 0.09 | 0.09 |
| Fragrance | 0.25 | 0.25 | 0.25 | 0.25 | 0.25 | 0.25 |
| pH Adjust to 6.5-7.1 w/ Citric Acid or Potassium Hydroxide | | | | | | |
| Lather Volume, ml | 271 | 245 | 297 | 261 | 288 | 277 |
| Lather Texture, grams | 14 | 13 | 17.7 | 17.1 | 16.6 | 17.3 |

| | Syndet Formulations | | | | |
|---|---|---|---|---|---|
| | Comp S % Active | Comp T % Active | Comp U % Active | Comp V % Active | Comp W % Active |
| DI Water | 66.5409 | 66.8109 | 68.939 | 69.329 | 71.3409 |
| Tetrasodium EDTA | 0.05 | 0.05 | 0.05 | 0.05 | 0.05 |
| Sodium Lauroamphoacetate | 3.36 | 3.36 | 3.36 | 3.36 | 3.36 |
| Methycellulose | 0.5 | 0.5 | 0.5 | 0.5 | 0.5 |
| Glycerin (Porcine-Free) | 4 | 4 | 4 | 4 | 4 |
| Lauric Acid | 1.42 | 1.42 | 1.42 | 1.42 | 1.42 |
| Myristic Acid | 1.96 | 1.96 | 1.96 | 1.96 | 1.96 |
| Stearic Acid | 0.54 | 0.54 | 0.54 | 0.54 | 0.54 |
| EGDS | 0.5 | 0.5 | 0.5 | 0.5 | 0.5 |
| $C_{10}$ acyl glycinate | | | | | |

TABLE 4-continued

Syndet Prototypes with Lather Volume @ 15 sec <300 mL and Lather Texture <20 g - Non-inventive compositions

| | | | | | |
|---|---|---|---|---|---|
| $C_{12}$ acyl glycinate | 0.79 | 1.57 | | | |
| $C_{14}$ acyl glycinate | | | 8.605 | 11.474 | 15.72 |
| $C_{12}$ acyl glutamate | | | 9.776 | 6.517 | |
| $C_{14}$ acyl glutamate | 19.99 | 18.94 | | | |
| Acyl glutamate/acyl glycinate ratio | 25.44 | 12.05 | 1.14 | 0.57 | 0 |
| MIT | 0.0091 | 0.0091 | 0.0091 | 0.0091 | 0.0091 |
| Potassium Hydroxide | 0.09 | 0.09 | 0.09 | 0.09 | 0.09 |
| Fragrance | 0.25 | 0.25 | 0.25 | 0.25 | 0.25 |
| pH Adjust to 6.5-7.1 w/ Citric Acid or Potassium Hydroxide | | | | | |
| Lather Volume, ml | 270 | 272 | 214 | 199 | Formulation not soluble |
| Lather Texture, grams | 13.3 | 14.5 | 17.7 | 17.5 | Formulation not soluble |

Soap-Syndet Formulations

| Soap-Syndet Formulations | 14 - Inventive composition % Active | 15 - Inventive composition % Active | SLES-Betaine Soap Syndet (Dove Japan market formula) % Active |
|---|---|---|---|
| DI Water | 66.612 | 66.77 | 66.43 |
| Dequest 2010 | 0.05 | 0.05 | 0.05 |
| EDTA | 0.05 | 0.05 | 0.05 |
| Propylene Glycol | 1 | 1.00 | 1.00 |
| $C_{14}$ Guar | 0.2 | 0.20 | 0.20 |
| Methycellulose | 0.4 | 0.40 | 0.40 |
| Glycerin | 2 | 2.50 | 2.00 |
| Lauric Acid | 4.43 | 5.14 | 7.70 |
| Myristic Acid | 7.58 | 7.32 | 8.70 |
| Stearic Acid | 2.03 | 2.12 | 2.80 |
| BHT | 0.05 | 0.05 | 0.05 |
| EGDS | 1.5 | 1.50 | 1.50 |
| Potassium Hydroxide | 3.279 | 3.20 | 4.31 |
| *$C_{10}$-$C_{14}$ acyl Glycinate | 1.34 | 1.77 | |
| $C_{14}$ acyl glutamate | 3.63 | 3.00 | |
| $C_{14}$ acyl glutamate/$C_{12}$ acyl glycinate ratio | 3.6 | 2.3 | |
| $C_{14}$ acyl glutamate/$C_{10}$-$C_{14}$ acyl glycinate ratio | 2.7 | 1.7 | |
| SLES | | | 2.80 |
| CAPB | 4.84 | 3.92 | 1.00 |
| Fragrance | 1 | 1.0000 | 1 |
| MIT | 0.00912 | 0.00912 | 0.00912 |
| Lather Volume, ml | 669 | 673 | 668 |
| Lather Texture, grams | 37.4955 | 42.3805 | 37 |
| Stearic Acid Replenishment (% remaining lipid) | N/A | 8.5 | 3.6 |
| Protein damage (% denatured) | N/A | 4.2 | 5.8 |

*$C_{10}$ - 10%, $C_{12}$ - 75% and $C_{14}$ - 15%

While this invention has been described with respect to particular embodiments thereof, it is apparent that numerous other forms and modifications of the invention will be obvious to those skilled in the art. The appended claims and this invention generally should be construed to cover all such obvious forms and modifications which are within the true spirit and scope of the present invention.

We claim:

1. A liquid personal cleansing composition comprising:
   a. 0.1 to 20% by wt. of individual surfactants or mixtures of $C_{10}$, $C_{12}$ and $C_{14}$ acyl glycinates;
   b. 2.0 to 20% by wt. of $C_{14}$ acyl glutamate;
   c. 1 to 25% by wt. of $C_8$ to $C_{24}$ fatty acid soap,
   in combination with other anionic, non-ionic or amphoteric/zwitterionic surfactants or mixtures thereof.

2. The composition according to claim 1, wherein amphoteric surfactant is present, and the amphoteric surfactant is sodium cocoampho monoacetate or diacetate.

3. The composition according to claim 1, wherein the zwitterionic surfactant is cocoamidopropyl betaine.

4. The composition according to claim 1, wherein the composition further comprises cationic conditioning polymers.

5. The composition according to claim 4, wherein the cationic conditioning polymer is guar hydroxypropyltrimonium chloride.

6. The composition according to claim 1, wherein the composition further comprises cellulose ethers that include methylcellulose (MC) or hydroxypropyl methylcellulose (HPMC) polymers.

7. The composition according to claim 1, wherein cations of $C_{10-14}$ glycinate and $C_{14}$ acyl glutamate are sodium, potassium, ammonium or substituted ammonium or mixtures thereof.

8. The composition according to claim 1 wherein the soap makes up 5 to 20% by wt. of the composition and is a $C_{10}$ to $C_{20}$ fatty acid soap and acyl glutamate makes up from 5 to 15% wt. of the composition.

9. The composition according to claim 1 wherein up to 75% by weight of the soap may be a potassium, magnesium or triethanolamine soap.

10. The composition according to claim 1 wherein the composition further comprises niacinamide, salicylic acid, vitamin C, retinyl ester or a sunscreen.

* * * * *